United States Patent
Hung et al.

(10) Patent No.: US 7,384,418 B2
(45) Date of Patent: Jun. 10, 2008

(54) METHODS AND DEVICES FOR DELIVERY OF AGENTS TO BREAST MILK DUCTS

(75) Inventors: David Hung, Belmont, CA (US); Phillip M. Olsen, Mountain View, CA (US)

(73) Assignee: Cytyc Corporation, Marlborough, MA (US)

( * ) Notice: Subject to any disclaimer, the term of this patent is extended or adjusted under 35 U.S.C. 154(b) by 728 days.

(21) Appl. No.: 10/721,701

(22) Filed: Nov. 25, 2003

(65) Prior Publication Data

US 2004/0147904 A1    Jul. 29, 2004

Related U.S. Application Data

(63) Continuation-in-part of application No. 09/313,463, filed on May 17, 1999, now Pat. No. 6,638,727.

(60) Provisional application No. 60/117,281, filed on Jan. 26, 1999.

(51) Int. Cl.
*A61K 9/22* (2006.01)

(52) U.S. Cl. .............................. 604/890.1; 604/891.1; 604/892.1

(58) Field of Classification Search ...................... None
See application file for complete search history.

(56) References Cited

U.S. PATENT DOCUMENTS

| | | | | |
|---|---|---|---|---|
| 3,845,770 A | * | 11/1974 | Theeuwes et al. | 424/427 |
| 4,838,862 A | * | 6/1989 | Baker et al. | 604/892.1 |
| 5,763,415 A | * | 6/1998 | Sukumar | 514/44 |
| 5,797,898 A | * | 8/1998 | Santini et al. | 604/890.1 |

OTHER PUBLICATIONS

Bolivar et al (Acta Radiologica, Mar. 1997, vol. 38, pp. 240-242).*

* cited by examiner

*Primary Examiner*—Karen A. Canella
(74) *Attorney, Agent, or Firm*—Theodore Allen; Mark Casey (57) ABSTRACT

The invention provides devices, kits and methods for delivering an agent to a breast milk duct. Intraductal agent delivery provides an opportunity to treat a breast condition locally and avoid the pitfalls of systemic drug delivery for a local condition. Time-released agents delivered into the ducts using an intraductal device or formulation reduces the frequency of intraductal administration required for desired efficacy over time. The methods include methods of treating a breast condition, including the conditions of cancer or precancer.

34 Claims, 9 Drawing Sheets

METHODS AND DEVICES FOR DELIVERY OF AGENTS TO BREAST MILK DUCTS

CROSS-REFERENCES TO RELATED APPLICATIONS

The present application is a continuation-in-part of U.S. application Ser. No. 09/313,463, filed on May 17, 1999 now U.S. Pat. No. 6,638,727, which claimed the benefit and priority of Provisional U.S. Application No. 60/117,281 filed on Jan. 26, 1999, under 37 CFR §1.78, the full disclosures of which are incorporated herein by reference.

BACKGROUND OF THE INVENTION

1. Field of the Invention

The field of this invention is delivery of agents to breast milk ducts.

2. Description of the Background Art

Drug delivery to breast cancer patients, and patients having other breast conditions requiring therapeutic intervention, has been limited to systemic administration of the prescribed drug, the clear disadvantage of which is that the whole body is treated for a condition localized in the breast. Although systemic antibiotics for mastitis (infection in the breast duct) are reasonable treatments, and where the breast cancer has become metastatic, systemic administration is also reasonable, there are conditions that remain confined to the breast tissue and which would be most effectively treated by local administration.

Local surgical intervention is common in the treatment of localized breast cancer, as evidenced by the widespread practice of fine needle biopsies (FNAs), lumpectomy (breast lump removal), and partial mastectomy. Often following a lumpectomy or partial mastectomy, the breast tissue is radiated adjunctively. Such procedures generally disrupt the breast tissue, and in any event do not provide an opportunity for local delivery of a therapeutic agent to the breast.

Diagnostic procedures are being developed which involve collecting ductal fluid, in some cases by cannulating or catheterizing a breast duct to collect such fluid for cytological or marker analysis. Originally, retrieval of ductal fluid was facilitated by collecting the fluid from spontaneous nipple discharge, and later from nipple aspiration. Papanicolaou et al., (1958) *Cancer*, 11:377-409 describes exfoliative cytology from spontaneous nipple discharge of the human mammary gland and its value in the diagnosis of breast cancer. Goodson W H & King E B, *Chapter 4: Discharges and Secretions of the Nipple*, The Breast: Comprehensive Management of Benign and Malignant Diseases (1998) $2^{nd}$ Ed. Vol 2, Bland & Kirby Eds. W. B. Saunders Co, Philadelphia, Pa. pp. 51-74 describes nipple discharge and the ways in which it has been used to characterized conditions of the breast. Nipple aspirate cytology for the study of breast cancer precursors is described in King et al., (1983) *Journal of the National Cancer Institute* 71(6): 1115-21. Cytological epithelial hyperplasia and a typical hyperplasia diagnosed in nipple aspirate fluid are associated with increased risk of breast cancer in a study of 2701 women as described in Wrensch et al., (1992) *Am. J Epidemiology*, v. 135 (2): 130-141. Nipple aspirate fluid is identified as a promising non-invasive method to identify cellular markers of breast cancer risk in Sauter et al., (1997) *British Journal of Cancer* 76(4): 494-501.

Diagnosis using ductal fluid retrieved by accessing the duct with a lumen-based device such as a catheter or cannula is described by Sartorius et al., (1977) which proposed cytologic evaluation of breast fluid retrieved using hair-like single-lumen catheters for the detection of breast disease as described in *Journal of the National Cancer Institute* 59(4): 1073-80. Love and Barsky, (1996) *Lancet* 348(9033): 997-9 demonstrated retrieval of ductal fluid by breast-duct endoscopy using a single-lumen device to study stages of cancerous breast disease.

A company called Diagnostics, Inc. formed in 1968, produced devices to obtain breast ductal fluid for cytological evaluation. The devices included a nipple aspiration device to collect NAF from subjects, and single-lumen catheters to retrieve ductal fluid. The devices were sold prior to May 28, 1976, for the purpose of collecting breast ductal fluid for cytological evaluation.

Co-owned and copending U.S. patent application Ser. Nos. 09/067,661, filed Apr. 28, 1998, and Ser. No. 09/301,058 filed Apr. 28, 1999, and a corresponding PCT filed case describe and claim methods of ductal lavage using dual lumen catheters for infusing wash fluid through the infusion lumen and retrieving ductal fluid that mixes with the wash fluid and that is collected through a collection lumen of a dual lumen catheter. Co-owned and copending U.S. patent application No. 60/143,359 filed Jul. 12, 1999, describes and claims a dual lumen catheter for delivery and retrieval of ductal fluid for diagnosis. Co-owned and copending U.S. patent application No. 60/122,076 filed Mar. 1, 1999, (manifold) describes and claims a manifold device for lumen-based delivery of a therapeutic agent to multiple breast ducts on a single breast at the same time.

While cannulation and catheterization are suitable means for diagnostic retrieval of breast duct fluid, and also reasonable approaches to intraductal delivery of therapeutic agents, it would be a great advantage to improve upon the intraductal delivery devices and modalities available to patients having localized breast conditions for which the safest, least toxic and most effective therapeutic administration is intraductal.

The present invention improves upon existing and developing intraductal therapy by providing alternative intraductal delivery devices and modalities, and by extending the usefulness and practice of the presently known and described intraductal delivery modalities using ductal catheterization and ductal cannulation.

Relevant Literature

U.S. Pat. No. 5,763,415, to Sukumar discloses prophylactic and therapeutic methods of treating the ductal epithelium of a breast duct by treating the duct with an epithelium destroying agent, and claims a method of treating the ductal epithelium of a mammary gland prophylactically or therapeutically for cancer by ductal cannulation of a duct, and administration of a vector comprising thymidine kinase to the duct and its prodrug ganciclovir.

U.S. Pat. No. 4,981,692, to Popescu et al., discloses and claims a method of treating infections in an animal (particularly bovine animals) by administration of a therapeutically effective amount of aminoglycoside in liposome form by intramammary infusion.

U.S. Pat. Nos. 4,202,329 and 4,365,632, to Kortum disclose a process and apparatus for stimulating immune resistance by the introduction of at least one relatively small solid non-toxic substantially non-biodegradable body, having non-specific antigenic action, into each gland cistern of the udder. The continued presence of the non-specific antigenic body induces immune resistance including an increase in the number and activity of phagocytic cells in the udder, which in turn provides protection against bacterial invasion without degrading milk quality. U.S. Pat. No. 4,202,329 claims a method for inhibiting bacterial infection by use of this process and apparatus.

SUMMARY OF THE INVENTION

The invention provides methods of treating a breast condition by establishing a temporary access track to a breast milk duct and delivering an agent through the track to the duct over time wherein over a defined period of time a specific amount of agent is delivered at a relatively constant rate. Establishing a track can comprise placing an indwelling unit comprising a reservoir in the lactiferous sinus of the breast duct with a lead or tube (or tether or line) to the nipple surface for retrieving or reloading the unit. The invention also provides a method of treating a breast condition comprising placing an implant into a breast during breast surgery (the implant comprises a reservoir), and delivering an agent from the reservoir to the duct over time wherein over a defined period of time a specific amount of agent is delivered at a relatively constant rate. The invention also provides a method of treating a breast condition comprising accessing a breast milk duct and delivering an agent comprising a time-release formulation to the duct for delivery of the agent over time in the duct, wherein over a defined period of time a specific amount of agent is delivered at a relatively constant rate.

The invention provides devices for delivering an agent to a breast milk duct over time comprising placing an indwelling unit comprising a reservoir into a duct, or placing a unit at the nipple surface that has an access track into the duct (e.g., a tack-head configuration). A line, tether or tube can be connected to the reservoir to deliver agent to the duct (e.g., with the tack-head) or a line, tether or tube can be connected to an indwelling unit comprising a reservoir for the purpose or reloading or retrieving a spent indwelling unit. In either case, the reservoir in the unit (either indwelling or residing at the nipple surface) releases agent to the duct over time.

The agent delivered can be a therapeutically active agent, including e.g., any agent suitable for treating the breast condition identified, including e.g., any anti-cancer agents, any prophylactic agents, or any agent for treating any other breast condition or for prophylaxis against a breast condition. Thus, for example, the agent if an anti-cancer agent can include, e.g., an estrogen activity modulator, a cytostatic agent, or a cytotoxic agent. The agent may also include e.g., an antibody, a peptide, a polypeptide, a nucleic acid, a polynucleotide, a small organic molecule, a macromolecule, a polymer, a carbohydrate, or a lipid. The agent can be formulated to be released over time into a breast duct. The agent can be delivered to the lactiferous sinus of the breast duct for release into the rest of the ductal system from there, or the agent may be delivered to any part of the breast duct, e.g., including the ductal lumens of the ductal system and also the terminal ductal lobular unit.

The invention also includes kits having a device described herein for delivering an agent to a breast duct, and instructions for use of the kit. The kits can further include an agent or agents described herein for delivery to a breast duct.

DESCRIPTION OF THE SPECIFIC EMBODIMENTS

The following preferred embodiments and examples are offered by way of illustration and not by way of limitation.

The invention is a method of treating a breast condition comprising establishing a temporary access track to a breast milk duct; and delivering an agent through the track to the duct over time wherein over a defined period of time a specific amount of agent is delivered at a relatively constant rate. The breast condition can be any breast condition, for example breast precancer or cancer. Breast cancer proceeds through discrete premalignant and malignant cellular stages: normal ductal epithelium, a typical ductal hyperplasia, ductal carcinoma in situ (DCIS) (including low grade DCIS and high grade DCIS), and finally invasive ductal carcinoma. The line between cancer and precancer is defined differently in the field, but precancer can include those conditions up through low grade DCIS, and cancer can include high grade DCIS and invasive carcinoma. The breast condition (especially breast precancer or cancer) can be identified by mammogram, physical exam of the breast, MRI (magnetic resonance imaging), analysis of nipple aspirate fluid for abnormal cells, ductal lavage of the breast (e.g., as described in PCT/US 99/09141), or other means to identify the condition. Preferably the method of identifying the condition can provide information leading to which breast duct or ducts the condition is localized. The condition can arise in the breast duct lumen or in the terminal ductal lobular unit (TDLU).

Establishing a temporary access track to the breast duct can be accomplished in a number of ways. Temporary indicates a length of the duration of a treatment protocol, and can mean hours, days, weeks, months or years, or any period of time that is not considered permanent access to the duct. In a simple embodiment the access track can be a tube or lumen placed in the duct at the ductal orifice and extending down into the ductal lumen for a small distance (e.g., from about 5 mm to about 12 mm) providing a practitioner with a passage for catheter or cannula-based delivery of an agent on a regular basis. The access can be e.g., daily, weekly, or monthly or any interval of time suited to the dosage regime and the goal of facilitating an effective treatment (e.g., to arrest or eliminate the abnormal cells in the breast duct). Alternatively, a device may be placed in the duct at any position in the duct e.g., from the beginning of the duct near the ductal orifice down to and including the lobular ends of the ductal system, and any places in between. A preferred placement of the device, in some situations, will be placement of the device in the lactiferous sinus. Where a lesion is located within the duct, the preferred placement of the device may be at the site of the lesion or lesions. Where the device comprises also a line or tether that runs from the device in place in the duct to the nipple surface, a temporary access track is established for the duration of time that the device resides in the duct. The tether (line, tube or wire) attached to the device may further be detachable and/or removable, and also may be capable of being re-attached to the device when it is desirable to reload the device or remove it.

Establishing an access track can comprise placing an indwelling unit comprising a reservoir into the breast duct, (e.g., into the lactiferous sinus of the breast duct) with a line, tether, lead or tube to the nipple surface for retrieving or reloading the unit. Thus, an access track can comprise a tether, line, lead, tube or lumen connected to an indwelling unit that is delivered to the duct. Establishing an access track can mean a one-time access to the duct to deliver an indwelling unit (e.g., a pump or microchip) that is retrieved and/or reloaded later by use of the tether or line attached to the device. The indwelling unit once delivered to the duct can have an access line or lumen that extends to the exterior of the breast through the ductal orifice and that provides the ability to have access to the duct to retrieve the indwelling unit or to reload it. As mentioned, the tether or line may be detachable and then capable of reattachment later when it is time to reload or remove the device.

The agent is delivered through the track to the duct over time, e.g., over time after installation of the indwelling unit, or over time after installation of a tube in the duct for frequent access. Thus, for example an indwelling unit (e.g., one lodged in the lactiferous sinus of the duct or elsewhere in the ductal system and e.g., one having a tether or line to the outside of the duct through the ductal orifice for reloading or retrieval of a spent indwelling unit) delivers the agent into the ductal lumen over time. Over time means over a period of time, e.g., days, weeks, months, years, so that the therapy delivers more than one dose at one time, but rather the body and ductal cavity receives a sequence of doses to treat the condition. The agent is delivered to the duct over time which means that at one or more time points the agent is dispersed into the duct. For example, when the delivery is made by catheter through a tube lodged in the duct and having an opening flush with the nipple surface, over time including more than one time a delivery of an agent is made to the duct. Also further by example, where the agent that is delivered comprises a time-release formulation, a single delivery can effect a delivery over time where the agent that is originally delivered to the duct releases its contents into the duct in small aliquots to provide a treatment to the duct over time.

The agent that is delivered to the breast duct can comprise a time-release formulation. The agent itself may be formulated to release itself over-time and not all at once. Thus, for example a time-release gel delivered by catheter through a tube placed at the ductal orifice can be delivered to the duct in one administration, for a time-release dissemination of the agent throughout the duct. Similarly, other agents in such formulations or configurations as e.g., beads, capsules, sponges, polymers, or other formulation capable of providing a time-release of agent can be delivered through a tube in the duct accessible at the ductal orifice, e.g., by catheter or cannula.

Thus, over a defined period of time a specific amount of agent is delivered at a relatively constant rate to the duct. For example a time release formulation delivered to the duct through an access track created e.g., by a tube in the duct will release a specific amount of agent (e.g., $\frac{1}{10}$, $\frac{1}{100}$ or $\frac{1}{1000}$ of the agent delivered) at a relatively constant rate (e.g., each 1-12 hours, each 1-4 days, each 1-2 weeks, monthly, bimonthly) during the time that the formulation resides in the duct. Therefore concentration of agent, release rate can be manipulated in the formulation to provide the dosage and rate of release desirable for effective and safe delivery of the agent to the patient. Also for example, the agent can be contained in a device that can release agent at a constant rate, e.g., a pump or microchip programmed or engineered to deliver agent at a relatively constant rate. The pump or chip can be lodged in the duct fully and have a tether to the outside of the breast for reloading or retrieving the pump or microchip, or may reside on the nipple surface (or elsewhere on the breast) with a line or tube introduced into the duct (an access track) that provides the track for delivery to the duct. The rate of delivery of agent by the pump or microchip is most probably determined by the rate of release of agent from the pump or microchip that is engineered into the pump or microchip, and may also be effected by the concentration and/or amount of agent placed in the pump or microchip or other device for the purpose of agent delivery. The rate is relatively constant in that about X amount of agent is delivered over about Y amount of time.

As mentioned, establishing an access track can comprise placing an indwelling unit comprising a reservoir into the breast duct (e.g., into lactiferous sinus or elsewhere within the breast duct or TDLU) with a lead or tube (or tether or line) leading from the device to the nipple surface for retrieving or reloading the unit. The tether can be permanently attached to the unit or it can be removable and/or re-attachable, in either case e.g., for reloading or retrieving the unit later. The indwelling unit can comprise a pump, and the pump can be an osmotic pump. The pump can comprise a tack with a head wherein the head rests outside the duct, and a connected shaft penetrates the duct for delivery of the agent intraductally. The tack head can contain an osmotic or other type of pump. The pump, osmotic or otherwise, can be placed in the lactiferous sinus or elsewhere in the duct, e.g., also with a line or tether attached for reloading or retrieving a spent pump.

The pump mechanism can comprise e.g., a Duros™ osmotic pump, manufactured by Alza Corporation located in Palo Alto, Calif. The pump mechanism for intraductal administration can reside in the tack-head portion of the pump resting on the nipple surface, or it can comprise an indwelling unit that is placed into the duct. Below the tack-head of the pump can extend a tip, lumen, tube or shaft portion that is placed into a duct so that the pump delivers its agent into the shaft and thus into the duct. An indwelling unit placed into the duct may be a pump, e.g., an osmotic pump, and the pump may be placed into the duct at any position within the duct. The osmotic pump may be assembled or configured essentially as the pumps described in U.S. Pat. Nos. 5,531,736, 5,279,608, 5,562,654, 5,827, 538, 5,798,119, 5,795,591, 4,552,561, or 5,492,534, with appropriate modifications in size and volume for administration to the duct of a breast, e.g., for placement into the duct (e.g., the lactiferous sinus or elsewhere in the ductal system) or for placement on the nipple surface. The tip or shaft of a tack-head pump that resides on the nipple surface (the tip or shaft accessing the duct) may be able to rotate in order to accommodate ducts of various positions on the nipple surface. A single tack-head pump can have one or more tips or shafts placed below the tack-head in order to access a particular duct or ducts, e.g., where two or more ducts in a breast need to be accessed.

The pump once designed and configured, can be loaded with an appropriately formulated agent for intraductal administration. Once placed in the duct or on the nipple surface (with access to the duct) the pump may facilitate administration of a drug or therapeutic agent to the duct. Conceivably a tack-head pump may be configured to administer to all the ducts located in the breast of a given individual. A given breast may be fitted with several indwelling units, one each for any duct requiring treatment. Other pumps that can be used or may be adapted to intraductal administration can include, e.g., those described in Dash et al., *J Pharmacol Toxicol Methods* 40(1):1-12 (1998), Kim et al., *IEEE Trans Biomed Eng* 46(6):663-9 (1999), Bean C A, *Critical Care Nurs Clin North Am* 10(3):287-303 (1998). The pump may be made of biodegradable material and thus may degrade in the body after use, rather than be retrieved from within the duct. The indwelling units may have a line or tether attached or removable and re-attachable, e.g., for retrieving or reloading the unit.

The indwelling unit or unit residing on the nipple surface can comprise a microchip. The microchip can be shaped to suit its location in or on the duct, or other aspects of its function e.g., in a square, rectangular wafer, a semi-oval, a bead or other useful shape. The microchip can be made of a flexible malleable material, e.g., a plastic or polymer or silicone-based material that can be rolled and bent to accommodate the internal architecture of the lumen of a breast duct. For example, the microchip can be shaped in a semi-oval when flat and may have alternating cathode and anode ports spaced with ports having chemical agent that is released upon activation of the cathode and anode circuitry (see FIG. 7). The semi-oval or other shape can be rolled e.g., like a cocoon in order to be placed in the duct and reside there for release of the agent over time (see FIG. 8). The cocoon or other configuration of microchip can also comprise also a tether, line, or tube either for retrieving the spent microchip or for reloading it with chemical agent. The tether or line can be removable and may then also be re-attached at a later date for reloading and/or retrieving the unit. The microchip may be made of biodegradable material and thus may degrade in the body after use, rather than be retrieved. The microchip can release the agent over time upon activation of the microchip mechanism. A microchip can be placed in the lactiferous sinus or other part of the duct including e.g., the ductal lumen and/or the TDLU of one or more breast ducts. A controlled-release microchip is described in Santini et al., *Nature* 397(6717):335-8 (1999).

The invention provides a device for delivering an agent to a breast milk duct comprising a tube or shaft placed in the ductal orifice and extending for a length into the ductal lumen. The tube can reside in the orifice and extend into the duct, and can provide access to the duct by a lumen-based delivery device, for making periodic deliveries of an agent to the breast duct using the lumen-based delivery device that access the duct through the access track in place in the duct. The lumen-based delivery device can comprise a catheter or a cannula. Another alternative intraductal administration can comprise placing small hollow tubes in the openings of the duct and using these semi-permanent tubes (each having a port opening) as access units for accessing the duct on a routine basis (e.g., with lumen-based ductal delivery device, e.g., a needle, cannula or catheter) for administration of a liquid or semi-solid (e.g., a gel) formulation (containing e.g., a therapeutically active agent or a diagnostic agent) to the duct. The agent can be delivered the duct generally in a unit that spreads over time to the rest of the duct or most of the rest of the duct, or can be washed into the duct by a chaser following administration of a bolus of agent. Delivery can target the lactiferous sinus, provided the agent can be distributed to the part of the duct where it is needed to take effect, e.g., by diffusion throughout the duct over time. Optimally the agent may be delivered deeply into the duct, e.g., to the terminal ductal lobular unit of the ductal system. Minimally, the agent will contact any region of the duct at which abnormal cells, a lesion or tumor is present. Tube-like members can be placed in their respective ducts for facilitating regular catheter or cannula-based delivery of an agent to the duct. The tubes having an opening provide an easy access to the duct on a regular basis, e.g., daily, weekly or monthly, depending on the needs of the therapy.

The invention further provides a method of treating a breast milk duct comprising placing an implant into a breast during breast surgery; the implant comprises a reservoir having agent. The agent in the reservoir is delivered from the reservoir to the duct over time wherein over a defined period of time a specific amount of agent is delivered at a relatively constant rate. The reservoir can comprise a time release formulation or a biodegradable material. The reservoir can comprise a device e.g., a pump or microchip, or can comprise a unit of biodegradable material comprising agent e.g., a sponge, a polymer, a bead or set of beads, or other configuration of implant that can biodegrade during or after release over time of an agent. A device such as a pump or microchip can be attached to a line or tether that is thread to the nipple surface through the ductal orifice so that the device can be retrieved or reloaded later. The tether or line can be detachable, and may also be capable of being re-attached. The implant can be e.g., as disclosed in U.S. Pat. No. 4,711,251 which describes a body implantable lead. The implant can be e.g., as disclosed in U.S. Pat. No. 5,840,059 which describes an elongated flexible lasing transmission catheter. These same devices may be used as implants placed in the duct after surgery or to establish an access track to the duct by placing the device in the duct and retaining the lead to the nipple surface.

A breast cancer patient can be treated by excising a portion of abnormal tissue comprising a lesion (e.g., the lesion having precancerous or cancerous cells) and placing an implant in or near the region of excised tissue. The implant can comprise a delivery device or indwelling unit capable of delivering an agent to the breast after the surgery for a period of time. The device or unit can comprise e.g., a pump, a biopolymer implant, a gel, a time-release capsule, a microchip, a bead containing agent, or a sponge. The agent can comprise a therapeutic agent. Excising a portion of breast tissue can comprise performing a procedure such as, for example, a lumpectomy, a ductectomy, a partial ductectomy, an excision of a precancerous lesion, an excision of a cancerous lesion, a "J" excision or a "Y" excision. The implant can be retained in the breast after placement for a period of time in a range from about 1 month to about 24 months. The implant can have a tether, line, lead or tube that follows the duct to the ductal orifice at the nipple surface for retrieving a spent indwelling unit or reloading it. The tether or line can be detachable and/or capable of re-attachment.

The invention also provides a method of treating a breast condition comprising accessing a breast milk duct, and delivering an agent comprising a time release formulation to the duct for delivery of the agent over time in the duct. Over a defined period of time a specific amount of agent is delivered at a relatively constant rate. The time release agent can comprise a biodegradable material. The agent can be embodied in such shapes as e.g., a bead, a sponge, a capsule, or a plug, and such materials as e.g., a polymer, an organic material, a cream, or a gel. A biodegradable element that has agent bound-up or releasable from the composition of the element can be inserted into the duct to degrade therein and disseminate the agent bound-up in the element. Such an element can include e.g., a plug that is inserted into the lumen and degrades in the duct, beads that degrade in the duct (e.g., insertable by catheter or cannula), a sponge carrying agent, e.g., a sponge that expands and releases agent upon contact with ductal fluid, a capsule having agent for release in the duct, a polymer plug or implant, or a gel that can be delivered by catheter or cannula to the duct e.g., for time release therein (preferably the gel expands and moves in the duct to cover the maximum surface area of the ductal lumen possible).

The agent can be formulated in a solid shaft shape and the shaft can comprise a biodegradable polymer that slowly dissolves in the duct after placement in the duct, dispersing active agent over time. These solid shafts may be formulated of a slowly dissolving or disseminating material, e.g., a biocompatible, biodegradable, carrier housing a therapeutic agent for distribution in the duct. Over time, therefore, the shaft will shrink and eventually become nothing and need to be replaced with another therapeutic shaft. Over time the shaft shrinks as the agent is release from the shaft and dispersed into the duct including possibly regions of the duct, e.g., the sinus, the ductal lumen and/or the terminal ductal lobular unit. Alternatively, tube-like member is placed in a duct on nipple of the breast. A catheter-based delivery device having infusion mechanism can access the duct through a tube-like member by inserting distal tip from which agent is dispersed in the duct.

A solid shaft or plug may also be placed in the ductal orifice, e.g., a biopolymer implant for slowly dissolving and distributing a therapeutic agent that resides in the biopolymer matrix. See, e.g., Yapp et al., *Anticancer Drugs* 9(9): 791-6 (1998). The biopolymer implant may also be placed further down into the duct, for example in the lactiferous sinus, the ductal lumen and/or further into the duct (e.g., the terminal ductal lobular unit of the duct). The advantage of placing it at the orifice in a visible location is that it is clear when the implant is dissolved completely, which may indicate the timing of a replacement of the implant in the duct, or an opportunity to monitor the treatment of the condition to determine the optimal next time for administration and/or what the dosage should be or both.

The invention provides a device for delivering an agent to a breast milk duct over time comprising a reservoir capable of dwelling in the duct or on the nipple surface, and a line or tube connected to the reservoir to deliver agent to the duct, reload an indwelling reservoir when empty, or provide retrieval of an indwelling reservoir from the duct, wherein the reservoir releases agent to the duct over time. The empty indwelling reservoir can be reloaded through the line or tube. The reservoir can comprise a pump which can be e.g., osmotic. The reservoir can comprise a microchip. The reservoir can hold a volume of agent e.g., in the range of from about 0.001 ml to 10 ml. The reservoir can deliver a volume of agent at a rate in a range from about 0.0001 ml/day to about 0.001 ml/hour. Preferably the agent is concentrated and/or effective in minute amounts.

Figure 1:
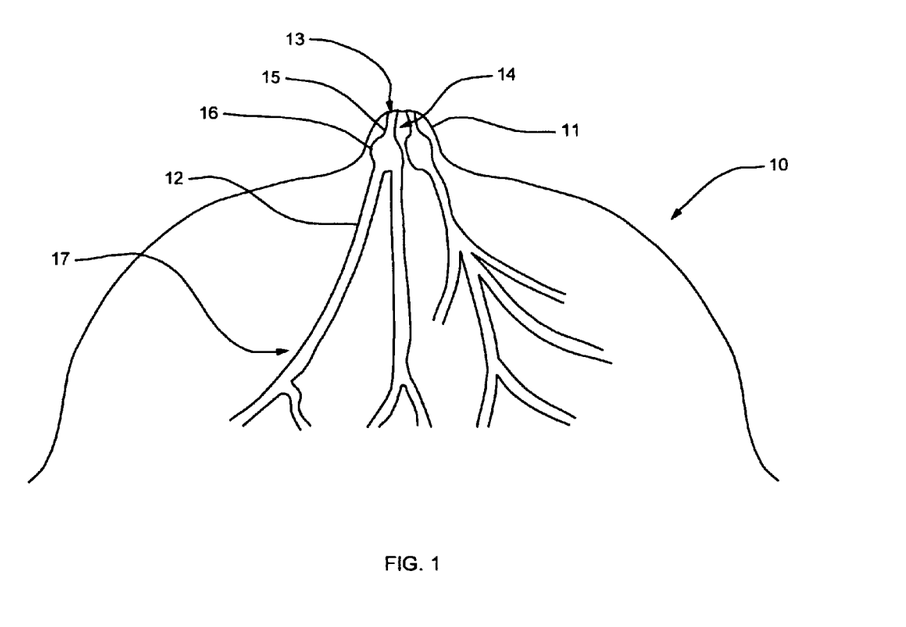
FIG. 1 shows a cross section of two breast ducts in a breast.
Figure 2:
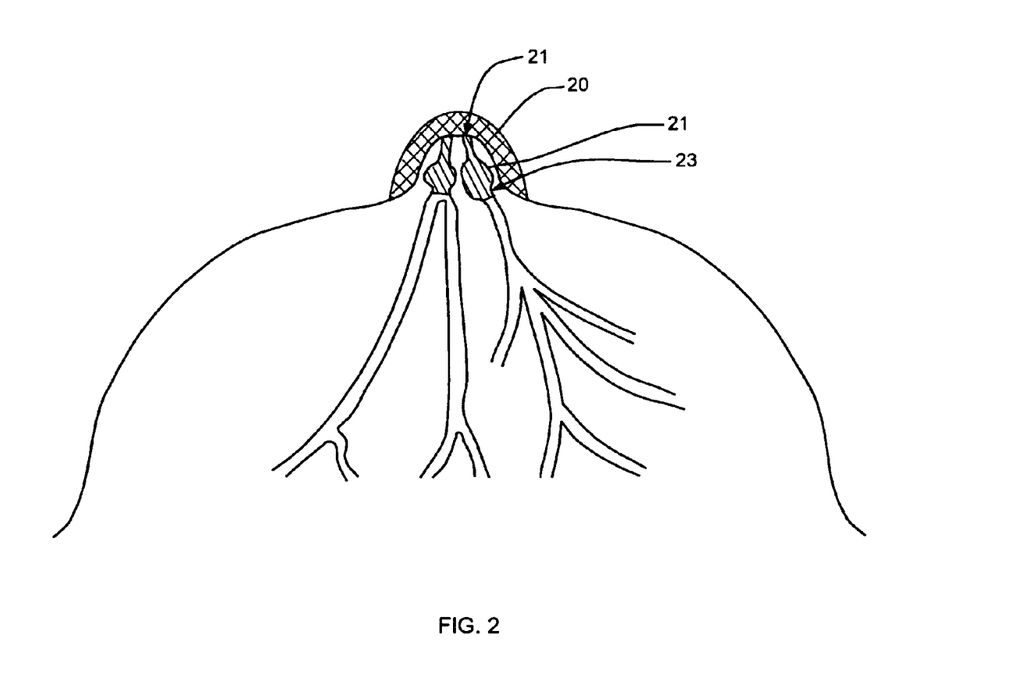
FIG. 2 shows an external delivery device accessing two breast ducts.

Turning now to the figures, FIG. 1 depicts the breast 10 having nipple surface 11, duct 12, orifice 13, lumen 14, sphincter of the lactiferous sinus 15, lactiferous sinus 16 and branching of the ducts 16. A device is introduced or an access track provided through orifice 13, and lumen 14, and the devices can reside in lactiferous sinus 15. FIG. 2 depicts a device in which the delivery mechanism 20 resides outside the duct and the device provides access members 21 connected to the delivery mechanism and residing in the duct for delivering the agent to the duct. The access members 21 can be designed to fit the lactiferous sinus 16 and have a nob 22 that is held by the lactiferous sinus sphincter 15, and tubes 23 to extend in the duct for delivery of the agent in the ducts 12. The external device 20 can be a pump, e.g., an osmotic pump. The pump can be a contained device, and the containment element can be made of a membrane or flexible material. Alternatively the containment element can be a more rigid material. The device can be affixed to the nipple by any means, e.g., by suction, an agent to affix to the nipple surface, tape or the like, or the attachment provided by the nobs 22 that hug the lactiferous sinus sphincters 15.

Figure 3:
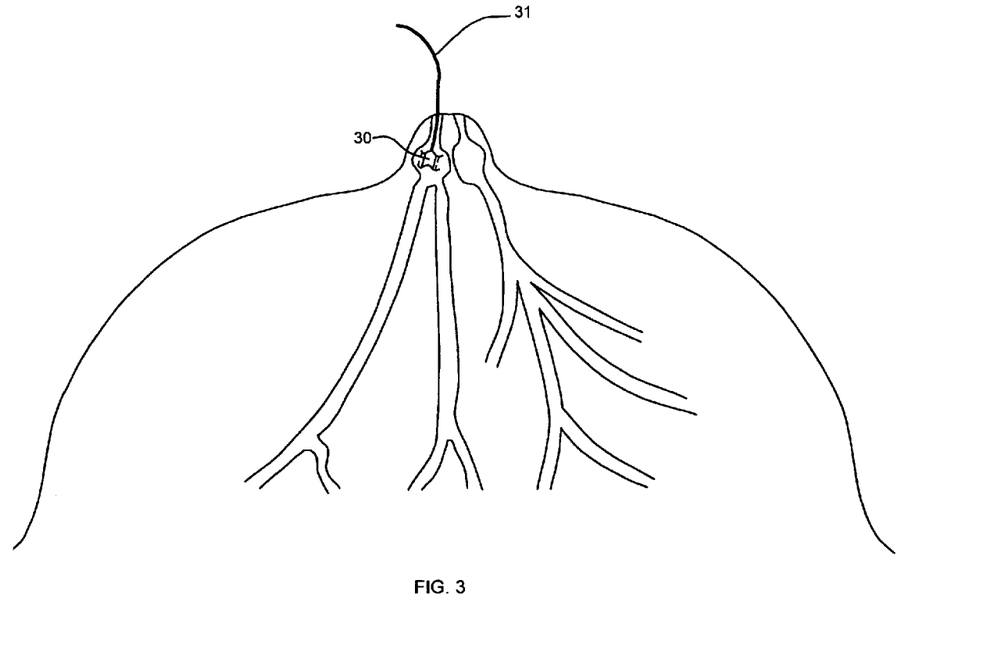
FIG. 3 shows an indwelling unit tethered and residing in a duct.

FIG. 3 depicts a indwelling unit 30 lodged in the lactiferous sinus 16 having a tether 31 that extends through the orifice 13 for reloading and/or retrieving the indwelling unit 30. The indwelling unit 30 is placed in the lactiferous sinus 16. The indwelling unit can be lodged at any place in the duct, and not necessarily just the lactiferous sinus. The indwelling unit can be any suitable delivery device having a reservoir that holds agent and a means for delivering an agent to the duct over time, e.g., the indwelling unit can be a pump or a microchip. The pump can be an osmotic pump. The microchip can be activatible once placed in the body, or just before placement. The tether 31 can be a line, or can be a tube having a lumen for delivery of the agent in the tube or lumen to reload or replenish the indwelling unit. The tether or line can be detachable, and also possibly re-attachable for later use or access to the unit. Preferably the indwelling unit 30 fits comfortably in the lactiferous sinus 16 (or other position in the ductal system) with room to disperse the agent, and yet is flexible or collapsible when spent for easy removal from the duct 12 through the lumen 14 and orifice 13.

Figure 4:
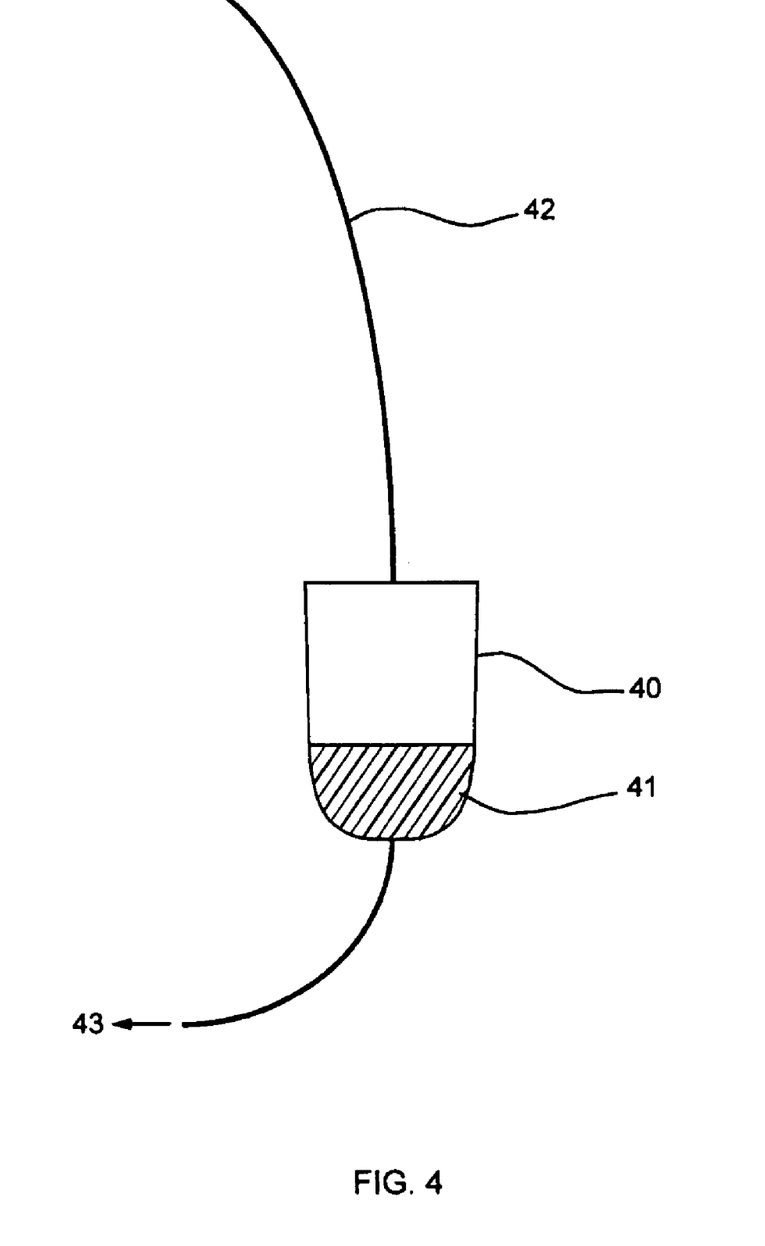
FIG. 4 shows an indwelling unit that is an osmotic pump having an atraumatic entry shape and having a tether to the nipple surface, residing in the duct.

FIG. 4 shows an indwelling unit osmotic pump 40 before placement in the duct. The pump 40 has an atraumatic front end 41 and a tether 42 for removal or reloading of the pump. Agent 43 is depicted in the pump, but may be in the pump in any way that suits the pump design and which facilitates the agent delivery to the duct.

Figure 5:
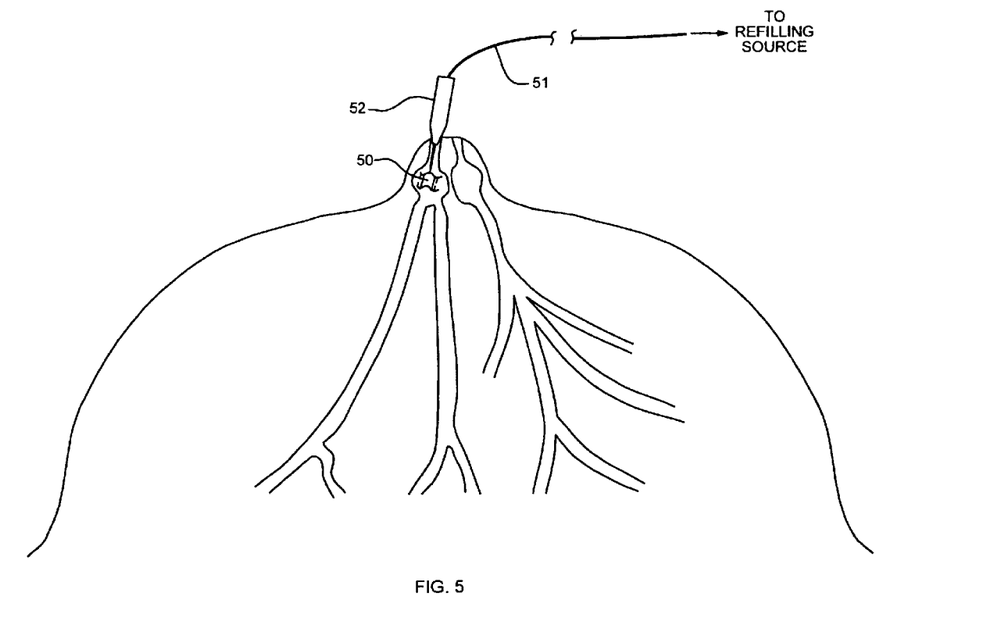
FIG. 5 shows catheter guided intraductal delivery of a tethered indwelling unit.

FIG. 5 depicts catheter-guided intraductal delivery of a tethered indwelling unit. The indwelling unit 50 is tethered with line 51 having a lumen that connects to a reloading source when the unit needs to be reloaded. The catheter 52 is designed to access the duct and deliver the unit into the lactiferous sinus for the duration of the treatment.

Figure 6:
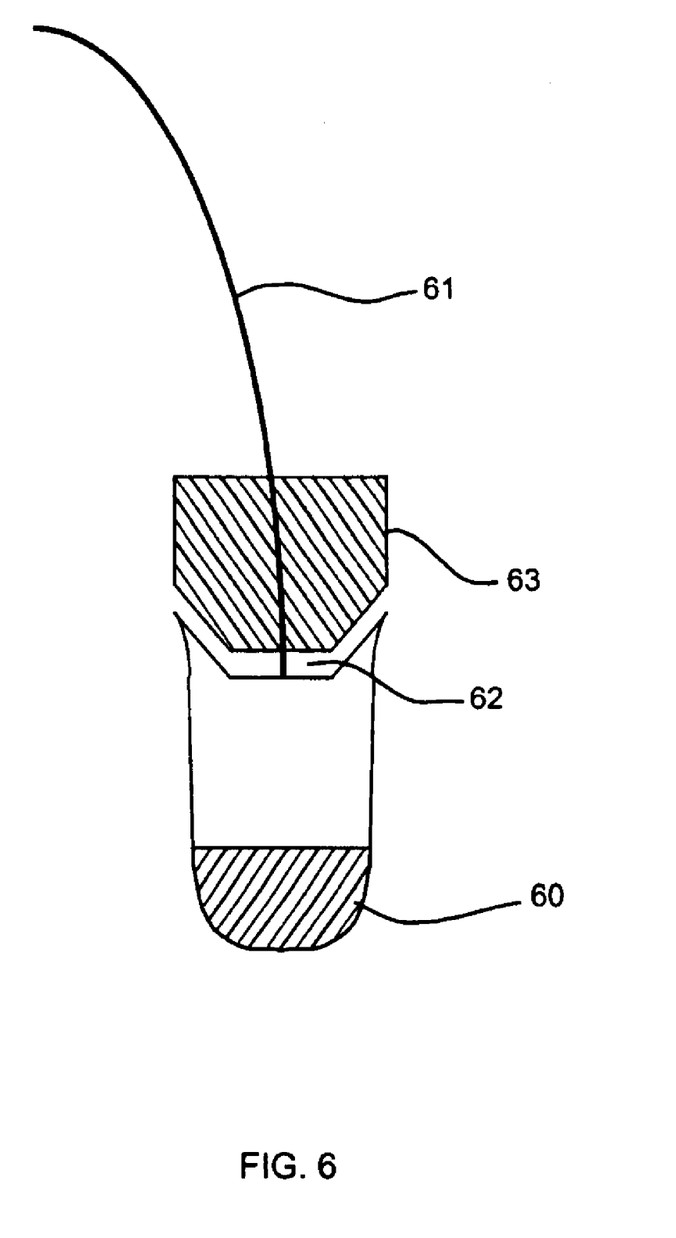
FIG. 6 shows integration of a catheter tip with an atraumatic indwelling unit.

FIG. 6 provides an indwelling unit 60 (e.g., a pump or a microchip) having attachment means 61 to attach to the catheter tip 63. The unit 60 when attached to the catheter tip 63 can access the duct and the catheter tip can push the unit 60 into the duct and lactiferous sinus. Thereafter, when the unit 60 is well positioned in the duct and/or sinus, the catheter tip 63 can release from the unit 60 and pull out from the tether 62 leaving a tethered unit in place for delivery of agent to the duct, and reloading or removal of the unit as desired after the agent is dispersed.

Figure 7:
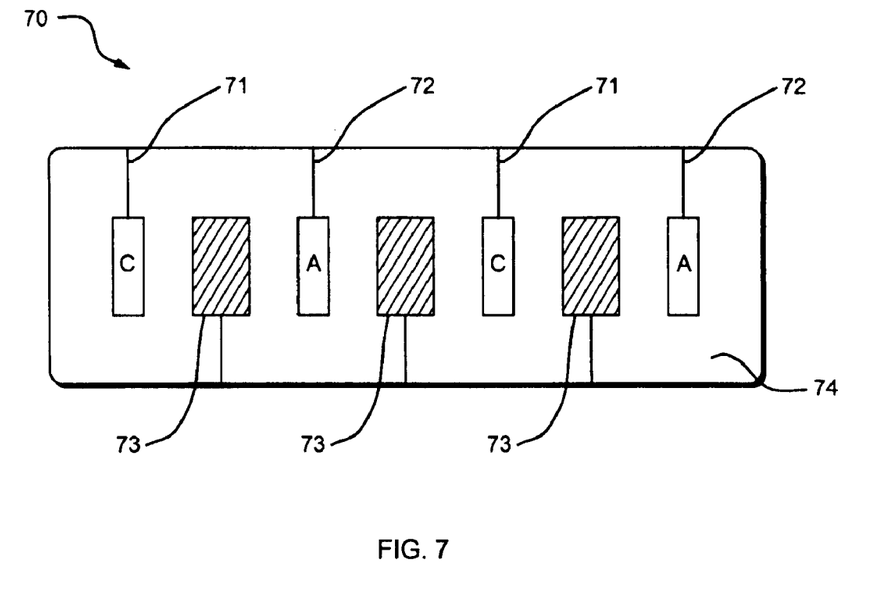
FIG. 7 shows circuit for a microchip for making a cocoon-type indwelling unit for intraductal delivery of an agent.

FIG. 7 depicts a circuit for a microchip 70. The circuit contains a cathode 71 and anode 72 members and wells 73 having chemical agent dispersible upon activation of the circuit 70 of the microchip. The material of the microchip on plane 74 can be silicon or other material suitable for the circuit and is preferably a flexible material that can adjust to the architecture of the duct or lactiferous sinus into which it is placed. Preferably also the material can be shaped after the circuit is filled e.g., in a cocoon or other atraumatic shape for delivery to the duct and while residing in the duct.

Figure 8:
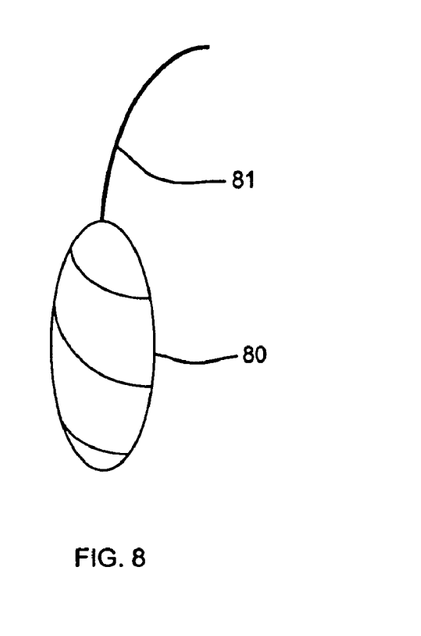
FIG. 8 shows a microchip in an atraumatic shape cocoon ready for delivery to a duct and having a tether for retrieval or reloading.

FIG. 8 shows a microchip 80 (e.g., a chip depicted in FIG. 7) in an atraumatic shaped cocoon ready for delivery to a duct and having a tether 81 for retrieval or reloading. The tether 81 can be a line for retrieving the microchip 80, or can contain a lumen for reloading and the tether 81 in that case would access the chambers of the microchip designed for holding the agent (see chambers 73 on FIG. 7).

Figure 9:
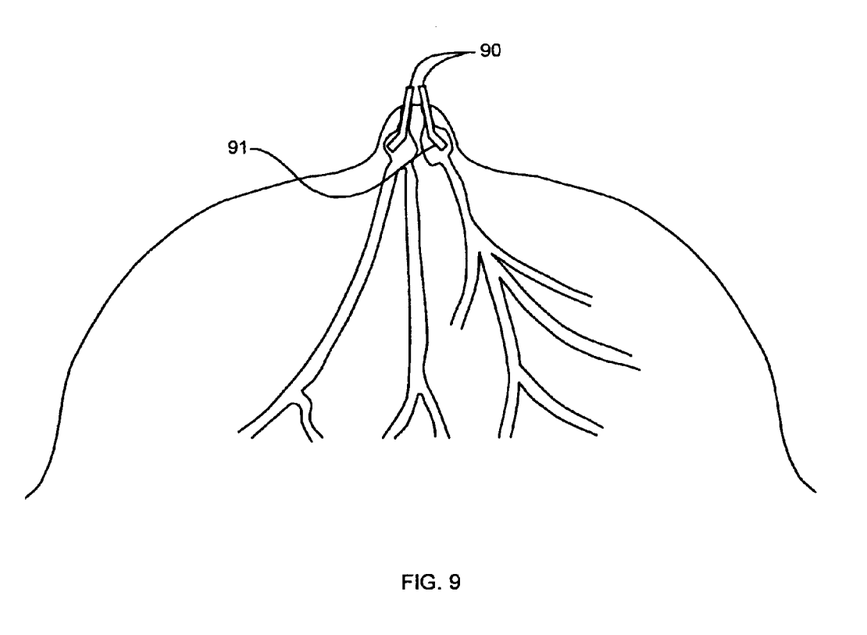
FIG. 9 shows biodegradable plugs in the ducts.

FIG. 9 shows biodegradable plugs (or shafts) 90 in the ducts. The plugs 90 can be straight rods, or as depicted here have a bend 91 to provide a holding means to hold the plugs 90 in place, e.g., by locking into the lactiferous sinus and/or the sinus sphincter. The plugs 90 can be made of a biodegradable material, e.g., a polymer or other biodegradable material for dispersing the agent into the duct at a relatively constant rate as the plug dissolves.

Figure 10:
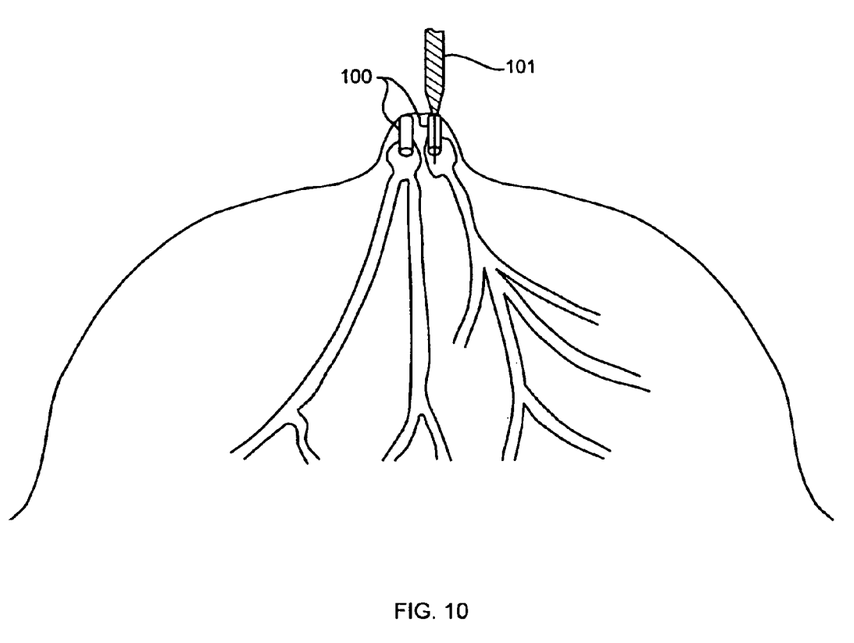
FIG. 10 shows tubes in the ducts for frequent access to the ducts with a catheter-like instrument.

FIG. 10 shows tubes 100 in the ducts for frequent access to the ducts with a catheter-like instrument 101. The tubes 100 can remain in the ducts for a period of time providing an access track for a catheter-based delivery of an agent to the duct. The agent can be, e.g., an agent formulated in a time-release formulation so that the agent once delivered to the duct disperses into the duct over time. Alternatively, the agent can be an agent that acts relatively immediately upon contact with duct. Using the access tracks established by the tubes 100, the agent can be delivered at a desired frequency to the duct, e.g., daily, weekly or monthly.

The invention further comprises a kit comprising a device comprising a reservoir and capable of dwelling in the duct or on the nipple surface, and a line, tube or tether connected to the reservoir to deliver agent to the duct, reload the indwelling reservoir when empty, or provide retrieval of an indwelling reservoir from the duct wherein the reservoir releases agent to the duct over time. The tether can be detachable from the unit and possibly also re-attachable for reloading or retrieving the unit. The kit can further comprise an agent for delivery using the device, e.g., the reservoir can be filled with the agent prior to placement in the duct. The kit also includes instructions for use of the kit contents, e.g., assembly or loading of an indwelling unit or unit residing on the nipple surface, approximate delivery rates using the devices or possible ways to modify the delivery rates, directions for positioning the unit or implant into or upon the duct, and how to determine where to place the unit, and the like. The instructions may be generally patterned after the information disclosed herein in discussions about the methods of the invention, where appropriate.

An agent for treating a breast condition by delivery of the agent to a breast milk duct can comprise a formulation selected from the group consisting of a liquid, a gel, a foam, an aerosol, a powder, a capsule, a sponge, a biodegradable polymer, a biodegradable material, a bead, and a liposome. The agent can be delivered to the lactiferous sinus or other part of the duct, e.g., the ductal lumens or branches or the terminal ductal lobular unit (TDLU). The agent can be delivered by a device selected from the group consisting of a gun, a syringe, a lumen-based delivery device, an aerosol-based delivery device, and an external pump. The agent once delivered to the breast duct in the formulation can be released into the duct over time. The agent can comprise a molecule selected from the group consisting of an antibody, a peptide, a polypeptide, a nucleic acid, a polynucleotide, a small organic molecule, a macromolecule, a polymer, a carbohydrate, and a lipid.

Various formulation modalities are available for delivery of an agent to the lactiferous sinus; among the illustrated modalities are deliverable to any part of the ductal system appropriate including e.g., intraductal sponge, beads containing agent, a polymer implant, a gel, and a capsule. Collagen, liposomal, or other types of delivery beads can be lodged in the sinus, ductal lumens, branches or TDLU for dissipation of the therapeutic agent in the beads. A duct may have a polymer implant placed in it for dissolving over time to release the agent housed in the polymer over time into the breast duct system. A duct may have a biocompatible, biodegradable polymer gel distributed to at least a portion of the duct.

The time-release capsule can be placed in a location within some portion of a breast milk duct. The capsule can be biodegradable and/or a time release capsule. The time-release capsule can be formulated e.g., using an estrogen activity modulator as the active agent essentially as described in U.S. Pat. No. 5,676,972 or 5,613,059. The time release capsule so formulated and administered intraductally, may also contain e.g., a cocktail of two or more agents for an appropriate therapeutic purpose for treatment precancer or cancer in a duct, as can any agents delivered by any modality described herein.

Any of the agents for any of the local deliveries described herein can be formulated e.g., in a liquid form, a gel, a cream, a liposome formulation, a polymer, a time-release formulation, a solid, and any other formulation appropriate for the particular local delivery. The liposome formulation can comprise liposomes such as described e.g., in WO 96/14864, WO 97/38731, U.S. Pat. Nos. 5,512,294, 5,527,528, EP 36,277, WO 83/02069, and U.S. Pat. No. 5,077,057. The agent can be a diagnostic agent or a therapeutic agent. The formulation can include e.g., a liquid, a gel, a foam, an aerosol, a powder, a capsule, a sponge, a biodegradable polymer, a biodegradable material, a bead, or a liposome. The agent can be delivered to any place in the breast duct. The agent can be delivered by a device selected from the group consisting of a gun, a syringe, a lumen-based delivery device, an aerosol-based delivery device, and an external pump. The agent can be delivered to the breast duct in the formulation that is released into the duct over time. The agent can comprise a molecule selected from the group consisting of an antibody, a peptide, a polypeptide, a nucleic acid, a polynucleotide, a small organic molecule, a macromolecule, a chemical, a polymer, a carbohydrate, and a lipid.

Therapeutic treatment can be specifically directed to the sick cells or molecules by use of a targeting molecule conjugated to a therapeutic agent. Targeting agents can include compounds or substances (such as antibodies, drugs, chemicals, etc.) that bind specifically to become incorporated into or in some fashion serve as a vehicle for identification of cell types of interest. Targeting agents for the present invention can include e.g., intraductal cellular targets including Her2 (EGF receptor) or any ligand or receptor of the ErbB family, any heat shock protein (HSP), such as heat shock protein 27 and the like; cytokeratins (particularly keratin 14); estrogen and progesterone receptors (or any androgen or other steroid receptor); cathepsins, including cathepsin-D; growth factors/cytokines including FGF1-18, VEGF, IGF-I, IGF-II, PDGF, KGF, EGF, PLGF, HGF, TNF, TGF alpha, TGF beta and the like; growth factor receptors to FGF1-18, VEGF, IGF-I, IGF-II, PDGF, KGF, EGF, PLGF, HGF, TNF, TGF alpha and beta and the like; urokinase, urokinase-type plasminogen activator (UPA), plasmin, antiplasmin, UPA receptor (UPAR), fibrinogen, PAI-1 and 2, -chemokines (both C-C and C-X-C); integrins, selectins, cadherins, including alpha v beta 3; CEA, PSA, maspin, fas, fas ligand; collagenases, metalloproteinases, TIMPs, disrupted basement membrane epitopes, stromolysin-3-Ki-67, Ki-S1, p53, nm23, bcl-2, p21 ras, cyclins, pS2. Also included are antibodies generated from any of the active agents listed herein. Other targeting agents include e.g., small molecules, proteins/peptides, lipids, or nucleic acids. Certain antibodies chosen may themselves have both therapeutic as well as targeting capability. Such an example would include the monoclonal antibody to the Her-2 receptor as this is currently an approved therapy for breast cancer.

Therapeutically active agents can be any biologically active agents capable of achieving a desired therapeutic effect, such as killing or inhibiting proliferation of a neoplastic cell, for example. Exemplary bioactive therapeutically active agents include e.g., proteins, carbohydrates, nucleic acids, specifically including enzymes, antibiotics, anti-neoplastic agents, bacterio static agents, bacteriosidle agents, anti-viral agents, hemostatic agents, anti-inflammatory agents, hormones, anti-angiogenic agents, antibodies, and the like. Preferred therapeutically active agents for use in the present invention include chemotherapeutic small molecules (i.e., cyclophosphamide, adriamycin, tamoxifen, raloxifene, taxol, etc)-therapeutic proteins (i.e., Herceptin, maspin, andiostatin, endostatin, etc.)-genes/nucleic acids (p53, maspin, ribozymes against important cellular targets). These therapeutic agents optionally may be coupled to a wide variety of active agents or alternatively carriers, like liposomes or immunoliposomes for example, or biodegradable polymer formulations, for example for time release delivery.

Agents that can be delivered to a breast duct or to multiple breast ducts include any agent deemed to be effective to treat the condition identified in the breast. Thus, for example, if a patient is identified with breast cancer or precancer, an agent disclosed in U.S. Pat. No. 5,763,415, to Sukumar or its corresponding PCT publication WO 97/05898 may be delivered to a patient's breast intraductally in a selected formulation or delivery vehicle, delivered to the duct or ducts using the appropriate delivery device for that formulation or delivery vehicle.

Basic research in the molecular biology of breast cancer appears to be indicating that breast cancer can be responsive to administration with some form of estrogen activity modulator. See, Howell et al., (1998) *Recent Results Cancer Res* 152:227-244 ("The Primary use of Endocrine Therapies"). To reduce the cancer, the patient is administered an agent that blocks estrogen activity, either by modulating estrogen, its receptor, or by blocking estrogen synthesis. An estrogen activity modulator can comprise a class of agents selected from the group consisting of a selective estrogen receptor modulator (SERM), an estrogen antagonist, and a modulator of estrogen synthesis. The estrogen activity modulator can be tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. The soy isoflavone can be genistein or daidzein. The aromatase inhibitor can be torimifen or anastrozole.

Some possible candidate estrogen activity modulators are described in el Khissiin and Leclercq, (1998) *Steroids* 63(11): 565-74; O'Regan et al., (1998) *J Nat'l Cancer Inst* 90(20):1552-8; Favoni and Cupis (1998) *Trends Pharmacol Sci* 19(10): 406-15; Williams, G M (1998) *J Nat'l Cancer Inst* 90:1671; Huynh et al., (1996) *Clin Cancer Res* 2:2037-2042; England and Jordan (1997) *Oncol Res* 9:397-402; Ashby et al., (1997) *Regul Toxicol Pharmacol* 25:226-31, Long et al., (1998) *J Steroid Biochem Mol Biol* 67:293-304. In addition, estrogen activity modulators obtained from plants or foods can be used, including soy and soy isoflavones, including genistein and daidzein, as described in Xu et al., (1998) *Cancer Epidemiol Biomarkers Prev* 7:1101-8, Charland et al., (1998) *Int J Mol Med* 2:225-228, Franke et al., (1998) *Am J Clin Nutr* 68:1466S-1473S, Kim et al., (1998) *Am J Clin Nutr* 68: 1418S-1425S, Shao et al., (1998) *Cancer Res* 58:4851-7, Shao et al., *Journal of Cellular Biochemistry* 69(1):44-54, 1998; Liggins et al., (1998) *Anal Biochem* 264:1-7, Kinoshita et al., (1998) *Adv Exp Med Biol* 439: 1178-29, and Dees and Kennedy (1998) *Curr Opin Oncol* 10(6):517-522. Estrogen activity modulators that are aromatase inhibitors are described in Mor et al., (1998) *J Steroid Biochem Mol Biol* 67(5-6):403-411; Goss et al., (1999) *Oncology* 56(2):114-121; Coombes (1998) *Recent Results Cancer Res* 152:277-84; Costa et al., (1999) *Cancer* 85:100-3; Long et al., (1998) *J Steroid Biochem Mol Biol* 67(4): 293-304; and Lamb and Adkins (1998) *Drugs* 56(6): 1125-40. Gonadotropin hormone releasing agonists (GnRHA) are described at website www.amaassn.org/special/womh/newsline/reuters/03315440.htm (date 4-5-99); and in other publications including Jonat (1998) Br J Cancer 78 Suppl 4:5-8; Szamel et al., (1998) *Cancer Chemother Pharmacol* 42(3):241-6; Ciardo et al., (1998) *Minerva Ginecol* 50(1-2):25-29; Nagy et al., (1996) *Proc Natl Acad Sci USA* 93(14):7269-73; Burger et al., (1996) *Eur J Obstet Gynecol Reprod Biol* 67(1):27-33. The estrogen activity modulator can comprise an estrogen antagonist, an aromatase inhibitor, or a cocktail of estrogen activity modulators. The estrogen activity modulator can be an aromatase inhibitor e.g., torimefene, anastrozole (ZN 1033), letrozole (CGS 20,269), ICI 182, fadrozole hydrochloride (CGS 16949A), rivizor (also called vorozole), or 4-hydroxy-androstenedione (4-OHA, lentaron or formestane).

Other agents may also be delivered to the duct along with the therapeutic agent that provides the primary therapeutic benefit, e.g., a benefit to preventing or treating breast pre-cancer or cancer. Thus, for example, wound healing agents, antibiotics, or adjunctive therapeutic agents can be delivered by the methods and devices described herein.

The agent is to be delivered to the duct or ducts at an appropriate dosage, taking into account the patient size and relative overall health, the diagnosed condition and stage of the condition, the number of ducts being treated and whether both breasts are being treated, the rate of release of the drug being delivered in the particular time release formulation or time release delivery vehicle, the desired rate of release, the anticipated effectiveness of the drug per unit of drug, the desired daily dosage, the frequency or desirability of available readministration, and other relevant factors that might determine such a treatment decision as dosage for a drug delivered intraductally.

For example, the commercially available formulation sold by Zeneca Pharmaceuticals trademarked Nolvadex (tamoxifen) can be used at a dosage recommended by the manufacturer and the treating physician, e.g., a range of 10 mg to 40 mg of tamoxifen daily, optimally about 20 mg daily. An appropriate local dosage for the same drug, e.g., delivered intraductally, including e.g., as a liquid, capsule, gel, time release or other formulation might be an appropriate fraction of the systemic dosage, e.g., a range from $\frac{1}{2}$ to $\frac{1}{50}^{th}$ of the systemic tamoxifen daily dosage. Thus, a reasonable range of local dosage might be from 0.2 mg to 20 mg of tamoxifen, at the high end, and from 0.5 mg to 2 mg of tamoxifen at a middle level dosage and at a range from 0.01 mg to 1 mg of tamoxifen at a possible lower end of the extrapolated scale.

Where the local administration is not daily, but is e.g., a time release capsule, or weekly catheterization, the daily systemic dosage may be used as a benchmark for extrapolating a daily fraction to be multiplied by 7 (for 7 days in a week) or some other appropriate multiplier depending on the time-release period or the periodicity of the local administration. Thus, for example, a time release capsule having a delivery rate of about 0.2 mg daily to a duct, and a duration of 10 days, may be used. A weekly catheterization protocol may administer 20 mg in a time release gel that is then dispersed into the duct at a rate of about 3 mg per day. It is generally assumed in the calculation of a local dosage from a known advised systemic dosage that the local dosage can be less than the systemic dosage and will still have the same if not better effect in a breast milk duct. It is assumed the these local calculations are provided for on a per lesion basis, and apply to each duct having a lesion and requiring treatment. Thus, for example, the local dosage is doubled where lesions are located in two ducts, and, e.g., a time release capsule is administered to each duct having a lesion.

Comparative actions and assays for testing relative potency and effectiveness of various estrogen activity modulators especially with relation to estrogen receptor activity and other molecular events are described in Lu et al., (1998) *Breast Cancer Res Treat* 50:63-71, Jeng et al., (1998) *Endocrinology* 139:4164-74, Kurebayashi et al., (1998) *Oncology* S1:23-34, Celius et al., (1999) *Environ Health Perspect* 107:63-68, for purposes including determining relative dosages both for various estrogen activity modulator and for administration of a particular estrogen activity modulator extrapolated from systemic to local dosages. Dosages of other agents can be similarly determined.

EXAMPLES

1. Therapeutic Treatment of Precancerous Lesions in Two Breast Ducts of an Otherwise Asymptomatic Patient Using an Intraductal Osmotic Pump Placed in the Lactiferous Sinus of Each Duct A patient is diagnosed with precancerous lesions in two breast ducts (one duct in her right breast; one duct in her left breast) by retrieving the ductal fluid of multiple ducts on each breast and separately analyzing the fluid of each duct by cytology. The analysis revealed a ductal hyperplastic condition in the two suspect ducts. Each suspect duct was fitted with a small osmotic pump which was placed under local anesthetic into the subject ducts through the ductal orifice and ductal lumen into the lactiferous sinus of the duct which comfortably housed each osmotic pump mechanism. A small wire or thread is left protruding through the accessed duct to identify the pump, provide a means to reload it without removing the pump, and to provide a means to retrieve the pump at a later date. The pumps were filled with taxol at a high concentration that is dispersed in minute amounts over time by the pump action. The pump mechanism is tested by aspirating a small portion of the ductal fluid after pump installation to identify an expected amount of taxol in the ductal fluid. The ductal cells are re-analyzed by cytology periodically (i.e., once a month) by ravaging the duct and retrieving the lavage and ductal fluid, to identify whether the taxol is working, or whether the dosage or release rate needs to be increased or decreased.

2. Therapeutic Treatment of a Mammographically Negative, Cytologically Positive Cancerous Lesion in a Breast Duct by Biodegradable Polymer Implant Comprising Tamoxifen A postmenopausal woman who is mammographically negative had the ductal fluid of her breast ducts tested and a high-grade ductal carcinoma in situ lesion is identified by cytological analysis in one of her ducts. The duct size is estimated by using progressively bigger galactography needles to estimate the lumen size of the orifice and just below the orifice. A plug made of biodegradable polymeric material laced with high concentration of tamoxifen is made especially to fit the ductal lumen and orifice. The plug is introduced into the duct while the breast is under local anesthetic and pushed into the duct as deeply as possible, perhaps into the lactiferous sinus if the sinus is close enough and accessible enough to the ductal orifice and early lumen portion of the duct. The biodegradable polymer implant has an expected dissolving rate, after which another implant is placed in the duct, and so on. In between polymer replacements, the ductal fluid is tested for progress in reducing the serious condition therein. The dosage of local tamoxifen is increased upon a finding of no change or worsening. Upon a successive finding of no improvement, the drug introduced in the polymer implant is changed, e.g., to a cytotoxic agent, and further testing for progress ensues.

3. Therapeutic Treatment of a Precancerous Condition in Three Breast Ducts by Intraductally Administered Bead Microchips to the Three Affected Ducts for Time Release Administration of a Drug to Last Six Months A patient in her 30s is diagnosed with three breast ducts having a typical ductal hyperplasia after ductal lavage of ducts that yielded fluid upon nipple aspiration. Two ducts are on the right breast, and one duct is on the left breast. Several bead microchips are prepared for each breast duct to be treated. The microchips release a highly concentrated formulation of a cytotoxic agent into the breast duct. The beads are administered to the breast ducts under local anesthesia using a single lumen cannula having a lumen large enough to pass one bead through at a time. The duct is dilated using progressively bigger galactography needles, in order to dilate the duct to be able to accept the cannula. The cannula is placed into the duct at a position estimated to be about the position of the lactiferous sinus. The beads are inserted into the duct using tiny puffs of air that release the beads into the cannula lumen and eject them into the lactiferous sinus. Each duct receives three beads. The ducts are monitored in situ using fluorescent dye-labeled antibodies to detect a rough quantitation of abnormal cells identified under fluorescent light. Unimproved or slowly improving ducts are administered one or two more beads. The body is monitored ensure that the cytotoxic agent is not detected systemically. Each bead lasts about four months, and thereafter is replaced at a dosage corresponding to the estimated amount of identified abnormal cells remaining in the duct.

4. Therapeutic Treatment of a Cancerous Lesion in a Breast Duct of a Patient by Intraductal Gel Administered Monthly to the Breast Duct Using a Fixed Administration Tube Placed at the Orifice of the Target Duct A breast duct on a patient's right breast is diagnosed with a low-grade ductal carcinoma in situ lesion. Under local anesthetic, the patient's duct is fitted with a hollow tube that is introduced into the ductal orifice after the orifice is dilated using galactography needles, and the tube is pushed into the ductal lumen until the end of the tube is flush with the nipple surface. The patient then receives a first administration of a biodegradable gel polymer filled with a cocktail of an estrogen activity modulator and a cytotoxic agent (e.g., faslodex and taxol). The amount of gel administered depends on the capacity of the lactiferous sinus and ductal lumens, and to the best extent possible the duct is filled with the gel. The dissipation time of the gel is estimated based on the concentration of therapeutically active agents in the gel and the volume of gel delivered to the duct. The patient is rescheduled for a readministration of more gel at the completion of that time period. The tube remains in place in order to facilitate the readministrations (which occur at approximately 3 to 6 weeks).

5. Adjunctive Therapeutic Treatment of Breast Cancer with Breast Implant Delivery Device Placed in the Breast of a Post-Surgical Women After Lumpectomy A lumpectomy is performed on a woman's left breast after detection of a palpable tumor. Breast cancer tissue and healthy tissue surrounding it is removed during the procedure. A breast reconstruction provides an implant under the muscle. The implant also contains a small osmotic pump device for delivering an anti-cancer agent to the breast in the region of the surgery, adjacent to the implant location. A lead wire from the pump is threaded into a nearby breast duct reaching the orifice, providing the opportunity to reload the pump when it empties in about three months.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device for delivering an agent to a breast milk duct over time, said device comprising: a unit for holding the agent to be delivered to the breast duct, said unit being sized and configured to be positioned and supported on a nipple, and an elongated member for delivering the agent from the unit to the breast duct, said elongated member being in communication with said unit, being sized for positioning within the breast duct, and having a distal terminal end for positioning within the breast duct, said distal end having an atraumatic tip.

2. The device to claim 1 wherein said unit comprises a reservoir for holding the agent to be delivered to the elongated member.

3. The device to claim 2 wherein said reservoir is sized to hold a volume of the agent in the range of from about 0.001 ml to 10 ml.

4. The device to claim 2 wherein said unit comprises a pump for delivering the agent from the reservoir to the elongated member when the elongated member is positioned within the breast duct.

5. The device of claim 4 wherein said pump is osmotic.

6. The device of claim 1 wherein said unit is capable of delivering a volume of the agent in a range from about 0.0001 ml per day to about 0.001 ml per hour.

7. The device of claim 1 wherein said unit comprises an osmotic pump for delivering the agent to the elongated member when the elongated member is positioned within the breast duct.

8. The device of claim 1 wherein said unit comprises a microchip for delivering the agent to the elongated member when the elongated member is positioned within the breast duct.

9. The device of claim 1 wherein said elongated member extends substantially perpendicular to a nipple engaging surface of the unit.

10. The device of claim 1 wherein said elongated member includes a portion for securely maintaining the elongated member within the breast duct.

11. The device of claim 10 wherein said portion of the elongated member includes a protruding member for engaging a wall of the breast duct.

12. A device for delivering an agent to a breast milk duct over time, said device comprising: a unit for holding the agent to be delivered to the breast duct, said unit being sized and configured for residing on a nipple surface, and an elongated member for delivering the agent from the unit to the breast duct, said elongated member being in communication with said unit, sized for positioning within the breast duct, having a distal terminal end for positioning within the breast duct, said distal end having an atraumatic end, and having a retaining member for holding the elongated member in the breast duct.

13. The device of claim 12 wherein said device includes an outer boundary that is shaped and configured for being fully supported on a nipple.

14. The device to claim 12 wherein said unit comprises a reservoir for holding the agent to be delivered to the elongated member.

15. The device according to claim 14 wherein said reservoir is sized to hold a volume of the agent in the range of from about 0.001 ml to 10 ml.

16. The device to claim 15 wherein said unit comprises a pump for delivering the agent from the reservoir to the elongated member when the elongated member is positioned within the breast duct.

17. The device of claim 16 wherein said pump is osmotic.

18. The device of claim 12 wherein said unit is capable of delivering a volume of the agent in a range from about 0.0001 ml per day to about 0.001 ml per hour.

19. The device of claim 12 wherein said unit comprises an osmotic pump for delivering the agent to the elongated member when the elongated member is positioned within the breast duct.

20. The device of claim 12 wherein said unit comprises a microchip for delivering the agent to the elongated member when the elongated member is positioned within the breast duct.

21. The device of claim 12 wherein said elongated member extends substantially perpendicular to a nipple engaging surface of the unit.

22. The device of claim 12 wherein said remaining member includes a protrusion for engaging a wall of the breast duct.

23. A device for delivering an agent to a breast milk duct over time, said device comprising: an indwelling unit for holding the agent to be delivered to the breast duct, said indwelling unit being sized and configured for being positioned and maintained within a portion of a breast duct, said indwelling unit having an atraumatic distal end for positioning within the duct, and an elongated member extending from said unit, wherein said elongated member can be positioned to extend out of said breast duct when said indwelling unit is positioned within the breast duct.

24. The device of claim 23 wherein said elongated member includes a tether that provides retrieval of the indwelling unit from within the breast duct.

25. The device of claim 23 wherein said unit includes a reservoir and said elongated member includes a lumen for delivering fluid to said reservoir when said reservoir is positioned within the breast duct.

26. The device of claim 23 wherein said elongated member includes an internal lumen for delivering a fluid to the indwelling unit.

27. The device according to claim 23 wherein said indwelling unit comprises a reservoir for holding the agent to be delivered to the breast duct.

28. The device of claim 27 wherein said reservoir is sized to hold a volume of the agent in the range of from about 0.001 ml to 10 ml.

29. The device of claim 28 wherein said indwelling unit comprises a pump for delivering the agent from the reservoir to the breast duct.

30. The device of claim 29 wherein said pump is osmotic.

31. The device of claim 23 wherein said indwelling unit is capable of delivering a volume of the agent in a range from about 0.0001 ml per day to about 0.001 ml per hour.

32. The device of claim 23 wherein said indwelling unit comprises an osmotic pump for delivering the agent to the breast duct when the indwelling unit is located within the breast duct.

33. The device of claim 23 wherein said indwelling unit comprises a microchip for delivering the agent to the breast duct when the indwelling unit is positioned within the breast duct.

34. A device for delivering an agent to a breast milk duct over time, said device comprising: an indwelling unit for holding the agent to be delivered to the breast duct, said indwelling unit including a microchip and being sized and configured for being positioned and maintained within a portion of a breast duct, said indwelling unit having an atraumatic distal end for positioning within the duct, and an elongated member secured to the indwelling unit, wherein said elongated member extends out of the breast when the indwelling unit is positioned within the breast duct.

* * * * *